(12) United States Patent
Grass et al.

(10) Patent No.: US 10,898,274 B2
(45) Date of Patent: Jan. 26, 2021

(54) MEASURING A LENGTH OF MOVEMENT OF AN ELONGATE INTRALUMINAL DEVICE

(71) Applicant: KONINKLIJKE PHILIPS N.V., Eindhoven (NL)

(72) Inventors: Michael Grass, Buchholz in der Nordheide (DE); Julien Senegas, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 102 days.

(21) Appl. No.: 16/314,939

(22) PCT Filed: Jul. 6, 2017

(86) PCT No.: PCT/EP2017/066954
§ 371 (c)(1),
(2) Date: Jan. 3, 2019

(87) PCT Pub. No.: WO2018/007531
PCT Pub. Date: Jan. 11, 2018

(65) Prior Publication Data
US 2019/0151030 A1    May 23, 2019

(30) Foreign Application Priority Data
Jul. 6, 2016  (EP) .................................. 16178114

(51) Int. Cl.
| *A61B 34/20* | (2016.01) |
| *A61B 5/06* | (2006.01) |
| *A61B 5/11* | (2006.01) |
| *G06F 3/01* | (2006.01) |
| *A61B 90/00* | (2016.01) |
(Continued)

(52) U.S. Cl.
CPC .............. *A61B 34/20* (2016.02); *A61B 5/061* (2013.01); *A61B 5/1114* (2013.01); *A61B 5/1122* (2013.01); *A61B 5/1128* (2013.01); *A61B 90/37* (2016.02); *G06F 3/017* (2013.01); *G06F 3/0304* (2013.01); *G06T 7/246* (2017.01); *A61B 5/749* (2013.01); *A61B 2017/00207* (2013.01); *A61B 2034/2055* (2016.02); *A61B 2034/2065* (2016.02); *A61B 2034/301* (2016.02); *A61B 2090/064* (2016.02); *A61B 2090/371* (2016.02); *A61B 2090/3735* (2016.02); *A61B 2090/3782* (2016.02); *A61B 2090/3937* (2016.02); *G06T 2200/04* (2013.01); *G06T 2207/10016* (2013.01); *G06T 2207/10028* (2013.01)

(58) Field of Classification Search
None
See application file for complete search history.

(56) References Cited

U.S. PATENT DOCUMENTS

| 2003/0187369 A1 | 10/2003 | Lewis |
| 2011/0118752 A1 | 5/2011 | Itkowitz |

(Continued)

FOREIGN PATENT DOCUMENTS

WO    2014093822 A1    6/2014

*Primary Examiner* — Dov Popovici

(57) ABSTRACT

A measurement system for measuring a length of movement of an elongate intraluminal device. Cameras are included to obtain three dimensional video data of movement of an elongate intraluminal device by hand. The video data is processed to track the movement of the elongate intraluminal device in three dimensions to provide the length measurement of movement of the elongate intraluminal device.

14 Claims, 2 Drawing Sheets

(51) Int. Cl.
*G06T 7/246* (2017.01)
*G06F 3/03* (2006.01)
*A61B 5/00* (2006.01)
*A61B 17/00* (2006.01)
*A61B 34/30* (2016.01)

(56) References Cited

U.S. PATENT DOCUMENTS

| | | |
|---|---|---|
| 2015/0164596 A1 | 6/2015 | Romo |
| 2015/0293596 A1 | 10/2015 | Krausen |
| 2015/0375399 A1 | 12/2015 | Chiu |
| 2016/0004315 A1 | 1/2016 | Morey | ion No. PCT/EP2017/066954, filed on Jul. 6, 2017, which claims the benefit of European Patent Application No. 16178114.1, filed on Jul. 6, 2016. These applications are hereby incorporated by reference herein.

FIELD OF THE INVENTION

The technical field generally relates to measuring a length of movement of an elongate intraluminal device, and more particularly to measuring a length of movement of a wire in an intravenous wire pullback method.

BACKGROUND OF THE INVENTION

Intravascular wire pullback measurements can be performed with a multitude of different sensors. These include pressure wires (iFR), intravascular ultrasound (IVUS), optical coherence tomography (OCT) and the like. Accurate registration of the wire based measurements with respect to the anatomy as it is visible from angiography projections profits from knowledge about the pullback length.

A pullback wire may be connected to a measurement device during pullback. For example, U.S. Patent Application Publication No. US 2003/0187369 discloses an optical pullback sensor assembly that facilitates measuring displacement of a flexible elongate member, such as an ultrasound catheter probe that is inserted within a body. The optical pullback sensor assembly includes a light source that illuminates a target surface that reflects at least a portion of light received from the light source. An optical sensor array including a set of sensor cells is arranged opposite the target surface to receive light reflected by the target surface. The optical sensor array is oriented to render image frames that are utilized to determine displacement of the flexible elongate member. A tracking guide on the pullback sensor assembly confines relative movement between the target surface and the optical sensor array in a direction of measured displacement of the optical sensor array. The measured displacement of the target surface in relation to the optical sensor represents displacement of the flexible elongate member.

Such a measurement system generally relies on a specific instrument and wire set-up and thus adds to complexity.

Other systems require interaction of a medical professional with user interface devices, which presents difficulties with respect to maintaining a sterile environment and sterile equipment.

Accordingly, an object of the present invention is to provide a way of measuring a length of movement of an intraluminal device without necessarily increasing complexity of the intraluminal device and whilst reducing any risk to sterility of a medical environment.

SUMMARY OF THE INVENTION

Hence, there may be a need to provide an improved and facilitated way of measuring a length of movement of an elongate intraluminal device.

The object of the present invention is solved by the subject-matter of the independent claims; wherein further embodiments are incorporated in the dependent claims. It should be noted that the following described aspects of the invention apply also for the measurement and processing system, the system, the imaging system and for the method as well as for the computer program element and the computer readable medium.

Methods, systems and computer programs are provided for measuring a length of movement of an elongate intraluminal device.

In one aspect, a measurement and processing system is provided for measuring a length of movement of an elongate intraluminal device, comprising a data receiver and at least one processor, wherein:

the data receiver is configured to receive video data from at least one camera of movement of the elongate intraluminal device; and the at least one processor is configured to process the video data to determine the length of movement of the elongate intraluminal device.

The measurement and processing system does not necessarily require a special elongate intraluminal device, since it obtains measurements from the video data at least of the elongate measuring device. Further, an analysis of video data to make the measurement does not require physical contact with a user interface, thereby assisting a sterile environment. The video data includes a part of the elongate intraluminal device that is extracorporeal (hereinafter also referred to as the "proximal part" of the device).

The video data may include at least one hand acting on the proximal part of the intraluminal device to move the intraluminal device. Thus, the at least one camera has a suitable sized and directed field of view.

The video data may be of the proximal part of the elongate intraluminal device and at least one hand acting upon the intraluminal device to move the intraluminal device. Thus, a medical professional is able to maintain a direct feel with the physical intraluminal device during a measurement procedure, as compared to virtual possibilities.

The at least one processor may be configured to determine a first position of the elongate intraluminal device from the video data and a second position of the elongate intraluminal device from the video data to determine the length of movement of the elongate intraluminal device. Such determination of first and second positions may be iterated to obtain discrete length measurements during movement of the intraluminal device. Thus, movement of the intraluminal device may be tracked as the procedure proceeds.

The video data may be three dimensional video data. Such three-dimensional video data takes into account that a medical professional may not move the intraluminal device along a single plane. Instead, the movement may have a component in three spatial dimensions, which can be tracked for accurate measurements.

The at least one processor may be configured to determine at least one position in three dimensional space of at least one reference point associated with the hand in the video data to determine the length of movement of the elongate intraluminal device. The reference point may for example be an optical marker or a natural landmark on the hand.

By tracking the reference point of the hand in the video data in three-dimensional space, the length of movement of the elongate intravascular device, in particular within the body, can be determined. The at least one processor may be configured to determine, at a set frame rate, positions in three dimensional space of the at least one reference point to track the movement of the elongate intraluminal device, which is used to determine the length of movement of the elongate intraluminal device. The length may be determined for each determined position movement.

The at least one processor is configured to determine a first position in three dimensional space of at least one reference point from a frame of video data and a second position in three dimensional space of the at least one reference point in a subsequent frame of video data and to determine the length of movement based on the first and second positions. These steps of determining first and second positions and determining length of movement are repeated to track movement of the intraluminal device using the video data.

The at least one processor may be configured to identify at least one of:

at least one hand gesture for indicating start of movement of the elongate intraluminal device;

at least one hand gesture for indicating end of movement of the elongate intraluminal device. Alternatively, the start and end of movement may be indicated by voice command.

The at least one processor may be responsive to the indication of start of movement or end of movement to initiate analysis of the video data to track movement of the elongate intraluminal device. Hand gestures and voice recognition provide a contactless user interface, which can aid ensuring a sterile environment.

The measurement and processing system may comprise the at least one camera. The camera may be adapted for obtaining three dimensional video data. The camera may be configured to pick-up infrared images.

The measurement and processing system may be adapted, through the at least one processor, to track a rotational movement of the elongate intraluminal device in the video data. For example, one or more reference points of at least one hand acting on the intraluminal device and/or on the intraluminal device itself may be tracked in three dimensional space using the video data to determine not only a length of movement of the elongate intravascular device, but also a measure of rotation thereof. A measurement of rotation of the elongate intraluminal device may provide useful information, particularly when combined with a directional sensor of the intraluminal device.

The data receiver may be configured to receive sensed information from a sensor of the elongate intraluminal device, and the at least one processor may be configured to register the sensed information to the determined length of movement. In this way, three-dimensional imaging of a bodily lumen or a profile of the sensed information as it varies with distance may be produced.

The at least one processor may be configured to register images from an extracorporeal imaging machine to sensed information from a sensor of the elongate intraluminal device using the determined length of movement. In this way, imaging, and display, of intraluminal sensed information in imaging data from the imaging machine is possible, such as registered intravascular and angiogram imaging data.

Image registration is one possible application of an output of the determined length and/or rotational movement measurement. Another possible application is to move a patient support platform or an imaging machine so that the intravascular device remains positioned within a field of view of the imaging machine as the intravascular device is moved.

A system is provided comprising the measurement and processing system and the elongate intraluminal device.

In various embodiments, the elongate intraluminal device comprises a sensor disposed at a distal end portion of a sheath, catheter or wire for sensing information of a bodily vessel.

An imaging system is also provided, comprising the measurement and processing system described above or the system described above and an extracorporeal imaging machine. The imaging machine may be an imaging machine for obtaining angiogram images.

The at least one camera may be physically associated with the extracorporeal imaging machine. The camera may be connected to a detector of the imaging machine. Usually, cameras associated with the detector are in position to view the intravascular imaging device and at least one hand of a medical professional.

A computer-implemented method is provided of measuring a length of movement of an elongate intraluminal device, the method taking place after positioning of the elongate intraluminal device within a bodily vessel, the method comprising:

obtaining video data from at least one camera of movement of the elongate intraluminal device; and processing the video data to determine the length of movement of the elongate intraluminal device.

The video data may include hand motion acting to move the elongate intraluminal device, and determining the movement of the intraluminal device is based on analyzing the hand motion in the video data.

A computer program element is provided for controlling a measurement and processing system as described above, the system described above or the imaging system described above when executed by at least one processor.

A computer readable medium is also provided having the computer program element stored thereon.

These and other aspects of the invention will be apparent from and elucidated with reference to the embodiment(s) described hereinafter.

DESCRIPTION OF THE DRAWINGS

The exemplary embodiments will hereinafter be described in conjunction with the following drawing figures, wherein like numerals denote like elements, and wherein.

DETAILED DESCRIPTION OF THE EMBODIMENTS

The following detailed description is merely exemplary in nature and is not intended to limit the application and uses. Furthermore, there is no intention to be bound by any expressed or implied theory presented in the preceding technical field, background, brief summary or the following detailed description.

Figure 1:
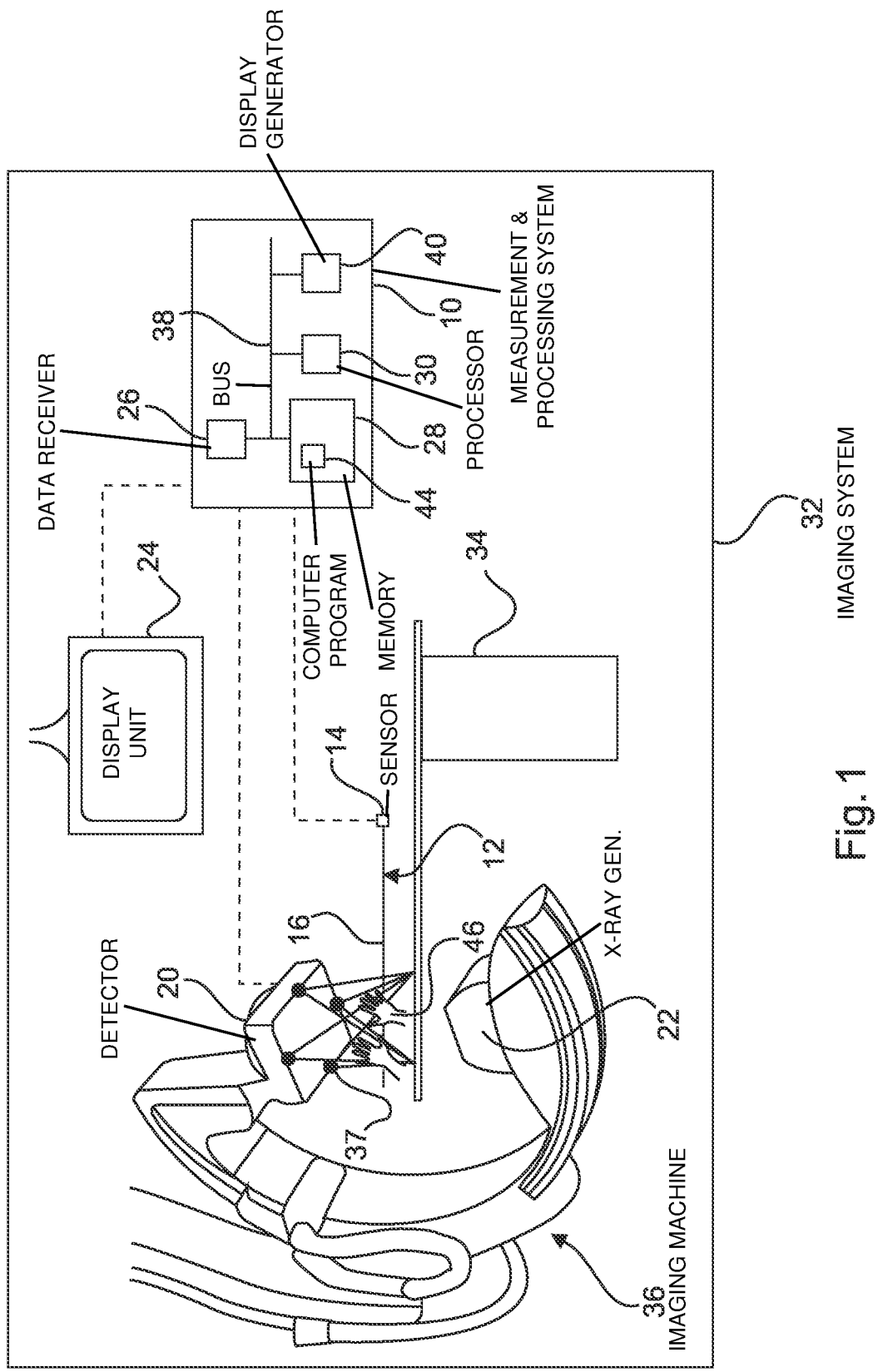
FIG. 1 is a schematic view of an imaging system in accordance with an embodiment.

FIG. 1 is a schematic view of an imaging system 32 comprising an extracorporeal imaging machine 36, a measurement and processing system 10, a display unit 24, an elongate intraluminal device 12 and a patient support table 34.

The imaging machine 36 is configured for generating imaging data of a patient supported on a table 34. The imaging machine 36 comprises a detector 20 and an electromagnetic wave generator 22 such as an X-ray generator. The imaging machine 36 may be configured for MRI imaging, X-ray imaging and the like. The imaging machine 36 may be configured for angiogram imaging. Further, the imaging data may be configured for generating three-dimensional imaging data. In a specific embodiment, the imaging machine 36 is a computed tomography (CT) imaging machine having a C-arm configuration, with the detector 20 at one end of the C-arm and an X-ray generator 22 at the other end of the C-arm.

The measurement and processing system 10, such as a general purpose computer, is operably connected to the imaging machine 36 and processes the imaging data from the imaging machine 36. The processed imaging data may be presented on the display unit 24 of the imaging system 32.

The measurement and processing system 10 comprises at least one processor 30. The processor 30 is operably connected to a memory 28. The processor 30 and the memory 28 may be connected through a bus 38. The processor 30 may be any device capable of executing program instructions, such as one or more microprocessors. The memory may be any volatile or non-volatile memory device, such as a removable disc, a hard drive, a CD, a Random Access Memory (RAM), a Read Only Memory (ROM), or the like. Moreover, the processor 30 may be embodied in a general purpose computer.

A display generator 40 is also operably connected to the processor 30 through the bus 38. The display generator 40 is configured to generate, with the processor 30, display of images for the display unit 24. The display generator 40 may be implemented by hardware, software or a combination thereof. The display generator 40 may be included as programming instructions for the processor 30 and stored on the memory 28. The display unit 24 may be any monitor, screen, or the like suitable for presenting a graphical user interface (GUI) capable of presenting medical images.

In the shown embodiment, the imaging machine 36 is operably connected to the processor 30. The imaging machine 36 obtains imaging data; which data is provided to the processor 30 for processing to create an angiogram or other imaging modality of a region of interest of a vascular system. The angiogram or other imaging modality may then be presented on the display unit 24.

The memory 28 has encoded thereon, at least one computer program 44 providing instructions which are executable by the processor 30 to process images from the imaging machine 36. In addition to the computer program 44 for processing the imaging data for presentation on the display unit 24, a computer program 44 is also provided that performs a method of measuring a length of movement of an elongate intraluminal device as described herein, particularly with reference to the flowchart of FIG. 2. The computer program 44 is also adapted to implement features of the processor, as described further herein.

The measurement and processing system 10 may be co-located with the imaging machine 36 or remotely located, or the measurement and processing system 10 may take on a distributed architecture.

The imaging system 32 comprises an elongate intraluminal device 12. The elongate intraluminal device may comprise an elongate member 16 and a sensor 14 located at a distal end portion thereof. The sensor 14 is configured to obtain sensed information, such as intraluminal images and intraluminal parameters, such as pressure. The sensor 14 may be an ultrasound imaging device, an optical coherence tomography (OCT) imaging device or a pressure sensing device, which are intraluminal sensing devices known in the art. The elongate member 16 may be embodied as a catheter or a wire. In particular, the intraluminal device 12 is an intraluminal sensing device that takes measurements during wire pull back. The device 12 is intraluminal in the sense that it is to be navigated through a bodily lumen of a human or animal subject, such as the esophagus, bowel lumens and particularly blood vessels. Such devices 12 are generally flexible and steerable to allow selective placement of the sensor 14 at a target site within the bodily lumen.

The elongate member 16 is arranged to be advanced or retracted (pulled back) by action of a medical professional on the physical elongate intraluminal device 12. The elongate intraluminal device 12 is configured to be navigated through a vascular network to a target site. In particular, a medical professional may grasp or pinch part of the elongate intraluminal device 12 to advance or retract it.

The elongate intraluminal device 12 is, in an exemplary embodiment, configured for pullback intraluminal measurements, whereby the sensor 14 is delivered to or beyond a target site in an intraluminal region of interest and is pulled back as measurements are being taken (e.g., imaging or pressure sensing). The resulting sensed information can be correlated to device displacement when the measurement and processing system 10, as further described below, is utilized.

The imaging system 32 comprises at least one camera 37 for obtaining video data. The at least one camera 37 is arranged to have a field of view covering at least one (user) hand 46 grasping a proximal end portion (located outside of the body) of the elongate intraluminal device 12. The at least one camera 37 is configured with the measurement and processing system 10 to determine a position of the at least one hand 46 when the at least one hand 46 is acting to move the elongate intraluminal device 12. The at least one camera 37 may comprise a plurality of cameras 37, which is four cameras 37 in the exemplary embodiment of FIG. 1, but other plural numbers are contemplated (e.g., three cameras 37).

The at least one camera 37 may be physically associated with the imaging machine 36. In the exemplary embodiment, the at least one camera 37 is connected to the detector 20, such as a flat detector panel 20 of the imaging machine 36. In an alternative or additional embodiment, the at least one camera 37 is connected to a lighting device that is articulable relative to the imaging machine 36.

The at least one camera 37 may be arranged to capture three dimensional video data. Thus, the at least one camera 37 allows a position in the obtained video data to be determined in three dimensional space (i.e., having x, y and z coordinates). For example, the cameras 37 may operate based on binocular or stereo imaging to determine depth and plane positions. In stereo imaging, two or more cameras 37 are used to capture two or more separate images from two or more different viewpoints, as shown in the exemplary embodiment of FIG. 1. In such systems, the location and optical parameters of each separate camera 37 are calibrated so that triangulation methods, as implemented by a computer program 44 running on the processor 30, can be used to determine the correspondence between pixels in each image. Alternatively, at least one projected-light camera 37 may be used that combines the projection of a light pattern with a standard 2D camera and that measure depth via triangulation. Another alternative is at least one time-of-flight camera 37 that measures depth by estimating the time delay from light emission to light detection, which may operate a modulated-light principle or (ii) a pulsed-light principle. Such cameras capable of determining three dimensional video data are known in the art.

The at least one camera 37 may obtain the video data in the visible range or the infrared range. The infrared range may allow for a clear differentiation of the at least one hand 46 from the surroundings due to human body temperature being elevated as compared to surroundings. In particular, the at least one camera 37 may be adapted to have a peak or relatively high spectral resolution at around 10 microns, corresponding to a peak intensity of infrared emission from the human body.

The measurement and processing system 10 is particularly adapted to implement (e.g., by a combination of at least one computer program 44 and at least one processor 30) for measuring a length of movement of an elongate intraluminal device 12, comprising a data receiver 26 and at least one processor 30.

The data receiver may be implemented by hardware, software (e.g., through a computer program 44) or a combination thereof. The data receiver is configured to receive video data of movement of the elongate intraluminal device from the at least one camera 37. The processor 30 is configured to process the video data to determine the length of movement of the elongate intraluminal device. In particular, the processor 30 may be configured to determine the length of movement of the elongate intraluminal device based at least on an analysis of hand motion in the obtained video data. The processor 30 may be configured to determine when the hand 46 is grasping or pinching the elongate intraluminal device 12, in which case motion of the hand 46 corresponds to movement of the elongate intraluminal device 12. The movement may be advancement or retraction of the elongate intraluminal device 12.

The hand 46 may move relative to the elongate intraluminal device 12 in order to reposition the hand 46 for successive movement operations of the elongate intraluminal device 12. In an example, the processor 30 is then configured to analyze the hand in the video data to distinguish between actual device movement, i.e., when hand 46 positioned on the proximal end of the device is moving the intraluminal device 12, and hand repositioning, i.e., when the hand is moving relative to the intraluminal device 12 for reposition purposes. Such analysis can be implemented, for example, by the processor being configured to distinguish between different configurations of the hand 46, such as a grasping configuration of the fingers used during device movement and a released configuration of the fingers used during hand repositioning. The system can be trained to make such distinction using, for example, machine learning techniques.

Alternatively or in addition, gesture or voice control may be applied as described further below to indicate when the elongate intraluminal member 16 is being grasped and when it has been released.

The processor 30 may be configured to total successive movement operations of the elongate intraluminal device 12, with each movement operation separated by repositioning movement of the hand relative to the elongate intraluminal device 12, in order to determine total length of movement of the elongate intraluminal device 12.

In an exemplary embodiment, the processor 30 is configured to determine a position in three-dimensional space of at least one hand 46 in the video data and/or the elongate intraluminal device 12 in the video data to determine the length of movement of the elongate intraluminal device 12. The position of the hand, specifically a reference point on the hand 46 such as an optical marker or a natural landmark, or the position of the elongate intraluminal device 12, specifically a reference point thereof, is determinative on the length of movement of the elongate intraluminal device 12 assuming recognition has been made that the hand 46 is grasping the elongate intraluminal device 12. The position of the hand 46 when acting upon the elongate intraluminal device 12 and/or the position of the elongate intraluminal device 12 can be tracked as it moves in the video data in order to determine the length of movement of the elongate intraluminal device 12. The processor 30 may be configured to algorithmically analyze the video data to track a point of the hand 46 (e.g., the tip of the forefinger) and/or the elongate intraluminal device 12.

In an exemplary embodiment, the video data is made up of frames as determined by a frame rate of the camera 37 when obtaining the video data. The processor 30 may be configured to track a reference point of the hand 46 and/or the elongate intraluminal device 12 on a frame-by-frame basis or on the basis of every predetermined number of frames. Specifically, the reference point of the hand 46 and/or the elongate intraluminal device 12 is determined in each frame or each predetermined number of frames. The position is usually a coordinate in three-dimensional space, for example a Cartesian coordinate. A length of movement of the hand and/or the elongate intraluminal device 12 can be determined by the processor 30 based on a change in position in three-dimensional space between frames for which the position has been determined, such as by using successive coordinates.

In various embodiments, the processor 30 is configured to determine a first position of the elongate intraluminal device 12 in the video data and a second position in a subsequent frame of the video data to determine the length of movement of the elongate intraluminal device 12 based on the distance between the first and second positions. The processor 30 may assume a linear path from the first to the second position to determine distance therebetween. For high frame rates, such an assumption is reasonable. The processor 30 may also be configured to determine at least one further position in subsequent frames of video data to determine the length of movement of the elongate intraluminal device 12 according to the analysis schemes described previously. For example, a frame-by-frame or every predetermined number of frames analysis may be performed by the processor 30 as described above.

Further, the processor 30 is configured to determine a rotational movement of the elongate intraluminal device 12 in the video data, preferably based on the analysis of the motion of the hand in the obtained video data, as well. For example, one or more reference points of at least one hand 46 acting on the intraluminal device, or alternatively on the intraluminal device itself may be tracked in three-dimensional space using the video data to determine not only a length of movement of the elongate intravascular device 12, but also a measure of rotation thereof.

For example, a path of movement of the one or more reference points can be tracked in three-dimensional space having x, y and z coordinated (where z coincides with a longitudinal axis of the intraluminal device 12). An arc of the path about the z axis can be determined in addition to a length of pullback movement along the z axis. The rotational movement determination can be separated from the length of movement determination or combined therewith. In a separation possibility, separate voice or hand gesture commands could be included for rotational manipulation of the intraluminal device 12 and for linear or pullback movements thereof, which can be recognized by the at least one processor 30 for instigating rotational and linear movement analysis respectively.

In various embodiments, the measurement and processing system 10 includes gesture control to determine start and end of movement of the elongate intraluminal device 12. These gestures may alternatively be phrased as gestures that are recognized to determine when the intraluminal device 12 has been grasped and when it has been released. The gesture control may include preset gestures with at least one hand 46. For example, a gesture from an open hand to a closed hand may correspond to start of movement and vice versa for the end of movement. Such gestures may also allow the processor 30 to determine when intraluminal device movement operations are being carried out and when the hand is moving relative thereto. The measurement and processing system 10 may be configured to output an acknowledgement of receipt of gestures, such as through the display generation module 40 and the display unit 24 or through audio feedback.

In addition to or alternatively to gesture control, the measurement and processing system 10 may include a microphone and the processor 30 is configured to analyze speech so that an operator can set the start and end of a movement operation of the intraluminal device 12 (or the initial grasping and release thereof).

The processor 30 and the display generator 40 are configured to correlate sensed information from the elongate intraluminal device 12, particularly the sensor 14 thereof, to the length measurements. Such information may be correlated to allow construction of a model of a bodily vessel from which the sensed information is obtained, with two dimensional images from slices obtained by the sensor 14 registered with accurate length information from the measurement and processing system 10 to construct a three-dimensional model. Additionally, or alternatively, the processor 30 and the display generator 40 are configured to construct a profile of the sensed information that varies over length of the bodily vessel based on the length measurement from the measurement and processing system 10. As explained previously, the sensed information may comprise pressure values, which relate to blood vessel flow. Changes in blood vessel flow may be indicative of various disease conditions. Alternatively, the sensed information may comprise imaging data obtained from the sensor 14, particularly imaging information of slices of the bodily vessel, which may also allow diagnosis of various disease conditions. Imaging modalities such as ultrasound and OCT are possible.

Additionally, or alternatively, the processor 30 and the display generator 40 are configured to register images from the extracorporeal imaging machine 36 with sensed information from the sensor 14 disposed at a distal end portion of the elongate intraluminal device 12 using the determined length of movement from the processor 30.

For example, the imaging machine 36 may obtain angiogram imaging data or other three-dimensional imaging data that can provide an overview three-dimensional map of a region of interest of the subject. An operator can use the imaging data from the imaging machine, which is displayed on the display unit 24, to position, by way of live tracking using the imaging machine, the elongate intraluminal device 12 at a target site within a vascular system of the region of interest. Sensed information can be obtained using the sensor 14 at the target site over a length of a bodily vessel, optionally using a pullback method. The length measurement from the measurement and processing system 10 and the sensed information from the sensor 14 can be correlated together and registered with the imaging data from the imaging machine 36 and integrated therewith in a to scale fashion and spatially registered way. The processor 30 and the display generator 40 are configured to generate the integrated imaging and display it on the display unit 24.

Image registration with imaging from the imaging machine 36 is one possible utility of an output of the determined length measurement. Another possible application is to move a patient support platform 34 or an imaging machine 36 so that the intravascular device 12 remains positioned within a field of view of the imaging machine 36 as the intravascular device 12 is moved. Thus, an output of the determined length and/or rotational movement has further utility. The processor 30 may send a command to the patient support platform 34 or the imaging machine 36 in response to the output to align the field of view of the imaging machine 36 and the moving intravascular device.

Figure 2:
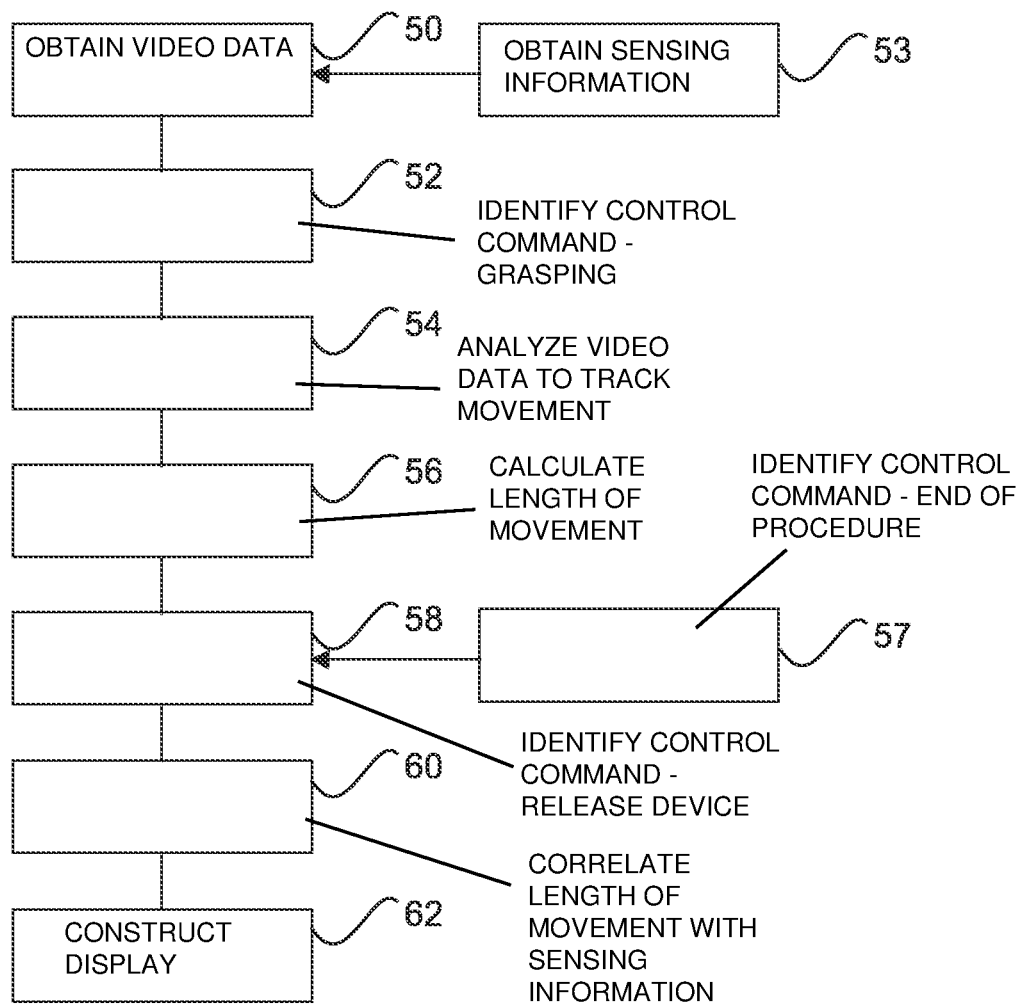
FIG. 2 is a flow chart of a method measuring length of movement of an intraluminal device.

A method of the present disclosure is described with reference to the flow chart of FIG. 2. It should be appreciated that computer implemented method steps described herein can be embodied in computer program instructions, which can be implemented by the processor 30. The method assumes that the intraluminal device 12 is already positioned in the vascular system of the subject on the table 34, optionally by way of live tracking of the intraluminal device 12 using the imaging machine 18, and thus does not necessarily include a surgical intervention on the subject.

In step 50, video data is obtained using the cameras 37. The video data is three-dimensional video data, allowing one or more reference points in the video data to be tracked in three dimensional space. The one or more reference points may be a tip of the finger or some other part of one or each of the hands 46, or an optical marker attached to a glove or directly to the hand, and optionally also, or alternatively, a part of the elongate intraluminal device 12.

In step 52, a control command indicating grasping of the intraluminal device 12 is identified by the processor 30. The identification may be performed by comparing the control command with a store of reference control commands in the memory 28. A gesture control command is, in an exemplary embodiment, identified in the video data from the cameras 37. For example, the hand 46 changing from an open hand to a closed hand may be a gesture control command that indicates grasping of the intraluminal device 12. In an alternative embodiment, a voice activated control command is identified by the processor 30, such as "start pullback".

Parallel to step 52 (or substantially parallel thereto) is step 53, which comprises commencing obtaining sensing information using the sensor 14 of the elongate intraluminal device 12. For example, imaging or pressure information may be obtained. Step 53 may be commenced responsive to the control command of step 52 or responsive to a different control command, which may again be voice or gesture based. The gesture based command may be identified in the video data. For example, "begin sensing" could be a voice activated control command or a hand gesture such as sticking out a thumb of the hand 46.

In step 54, the processor 30, responsive to the control command indicating grasping of the intraluminal device 12, begins a step of analyzing the video data to track movement of the intraluminal device 12. In particular, the processor 30 determines a position of one or more reference points in the video data associated with the hand and/or the elongate intraluminal device 12 on a frame-by-frame basis (or at a predetermined frame rate) to track the movement of the elongate intraluminal device.

In step 56, the processor 30 calculates length of movement of the elongate intraluminal device, which may also be performed on a frame-by-frame basis or at a predetermined frame rate, or it may be performed after a certain number of position determinations has been made according to step 54. The processor 30 may perform the length calculation based on a transformation from change in three-dimensional position to linear movement of the elongate intraluminal device 12.

In step 58, a control command indicating release of the intraluminal device 12 is identified by the processor 30. The identification may be performed by comparing the control command with a store of reference control commands in the memory 28. A gesture control command is, in an exemplary embodiment, identified in the video data from the cameras 36. For example, the hand 46 changing from a closed hand to an open hand may be a gesture control command that indicates releasing of the intraluminal device 12. In an alternative embodiment, a voice activated control command is identified by the processor 30, such as "end pullback".

Steps 52 to 58 may be iterated until a sensing and length measuring procedure is completed. A step 57 may be included in which end of procedure is determined based on a control command. The control command may again be based on a hand gesture identified from the video data, such as a horizontal sweeping motion of the open hand, or a voice control command such as "end procedure".

In step 60, the processor 30 correlates the length of movement measurement from the measurement and processing system 10 as obtained by steps 54 and 56 with sensing information from the sensor 14 of the elongate intraluminal device 12. The length of movement measurement may be a total length determination by accumulating advancement and/or retraction movements as determined by steps 54 and 56. Alternatively, each length determination according to step 56 may be correlated with the sensed information from the sensor 14 at a position in the bodily vessel corresponding to the length of movement.

In step 62, a display is constructed based on the correlated data from step 60. The display is constructed by the processor 30 and the display generator 40 for output on the display unit 24. The display may comprise a three-dimensional model of a bodily vessel based on sensed imaging information from the sensor 14 and the length of movement measurement from the measurement and processing system 10. Additionally, or alternatively, the display may comprise a profile of a sensed variable such as pressure, flow rate, cross-sectional area or diameter of inside of lumen of bodily vessel, etc. as it varies with position along the bodily vessel as determinable from the length measurements from the measurement and processing system 10. Additionally, or alternatively, the constructed display may comprise spatial registration and scaling of the sensed information, e.g., imaging data from the sensor 14, in the imaging data, e.g., angiogram imaging data, from the imaging machine 36. Such displays are useful for a medical professional in making an assessment of a disease condition such as stenosis, vessel narrowing, plaque build-up, thrombosis, etc.

It is possible, but not necessary, that imaging using the imaging machine 36 is carried out during movement of the intraluminal device 12 and sensing of information from a sensor of the intraluminal device 12. For example, an imaging procedure using the imaging machine 36 may be performed prior to start of a pullback procedure to determine a start position of the intraluminal device in the imaging data from the imaging machine. During pullback, the video cameras 37 and the processor 30 are configured to track hand-motion and to measure length of pullback of the intraluminal device 12. At the end of a pullback procedure, a further imaging process using the imaging machine 36 may be performed. A resulting path length measurement of moment of the intraluminal device 12 as describe above can be used to correlate sensed data from the sensor 14 with the imaging data from the imaging machine, e.g. angiogram imaging data.

In another exemplary embodiment of the present invention, a computer program is provided that is characterized by being adapted to execute the method steps of the method according to one of the preceding embodiments, on an appropriate system.

The computer program might therefore be stored on a computer, which might also be part of an embodiment of the present invention. This computer may be adapted to perform or induce a performing of the steps of the method described above. Moreover, it may be adapted to operate the components of the above described apparatus. The computer can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program stored on it which computer program is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program available for downloading is provided, which computer program is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the disclosure as set forth in the appended claims and the legal equivalents thereof.

For example, at least one optical marker (not shown) may be included on a hand (e.g. glove) 46 of a medical professional and/or on the elongate intraluminal device 12 to provide a reference point with improved contrast in the video data. Movement of the reference point in the video data in three dimensional space can be utilized to carry out the length measurements described herein.

In another example, plural optical markers may be included on the elongate intraluminal device 12 to further assist in tracking of the elongate intraluminal device 12.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A measurement and processing system for determining a length of movement of an elongate intraluminal device, comprising a data receiver and at least one processor, wherein:
   the data receiver is configured to receive video data from at least one camera, the received video data including motion of a user's hand interacting directly with the elongate intraluminal device to manually move the elongate intraluminal device; and
   the at least one processor is configured to process the received video data to determine the length of movement of the elongate intraluminal device based at least on an analysis of the motion of the hand in the received video data.

2. The measurement and processing system of claim 1, wherein the processor is configured to analyze the received video data so as to distinguish a movement of the intraluminal device from a repositioning of the hand relative to said device.

3. The measurement and processing system of claim 1, wherein the received video data is three-dimensional video data.

4. The measurement and processing system of claim 1, wherein the at least one processor is configured to determine at least one position in three dimensional space of at least one reference point associated with at least one hand in the received video data to determine the length of movement of the elongate intraluminal device.

5. The measurement and processing system of claim 1, wherein the at least one processor is configured to identify at least one of:
   at least one hand gesture for indicating start of movement of the elongate intraluminal device, and
   at least one hand gesture for indicating end of movement of the elongate intraluminal device.

6. The measurement and processing system of claim 5, wherein the at least one processor is further configured to determine a rotational movement of the elongate intraluminal device in the received video data, based on the analysis of the motion of the hand.

7. The measurement and processing system of claim 6, wherein the data receiver is configured to receive sensed information from a sensor of the elongate intraluminal device, and the at least one processor is configured to register the received sensed information to the determined length of movement.

8. The measurement and processing system of claim 7, wherein the data receiver is configured to receive images from an extracorporeal imaging machine, and wherein the at least one processor is configured to register the received images from the extracorporeal imaging machine to the sensed information from the sensor of the elongate intraluminal device using the determined length of movement.

9. A system comprising:
   the measurement and processing system for determining a length of movement of an elongate intraluminal device of claim 1; and
   the elongate intraluminal device.

10. The system of claim 9, wherein the elongate intraluminal device comprises a sensor disposed at a distal end portion of a catheter or wire for sensing information of a body vessel.

11. An imaging system comprising:
    the system of claim 9; and
    an extracorporeal imaging machine.

12. The imaging system of claim 11, wherein the at least one camera is physically associated with the extracorporeal imaging machine.

13. A computer implemented method of measuring a length of movement of an elongate intraluminal device, the method taking place after positioning of the elongate intraluminal device within a body vessel, the method comprising:
    receiving video data from at least one camera, the received video data including motion of a hand interacting directly with the elongate intraluminal device to manually move the elongate intraluminal device; and
    processing the received video data to determine the length of movement of the elongate intraluminal device based at least on analyzing the motion of the hand in the received video data.

14. A non-transitory computer-readable storage medium having stored thereon a computer program comprising instructions which, when executed on a computer, cause the computer to execute the method according to claim 13.

* * * * *